(12) United States Patent
Je et al.

(10) Patent No.: US 7,820,192 B2
(45) Date of Patent: Oct. 26, 2010

(54) METHOD FOR REMOTELY CONTROLLING A SOL-GEL TRANSITION OF HYDROGELS AND METHOD FOR DELIVERING A DRUG USING THE SAME

(75) Inventors: Jung Ho Je, Pohang-si (KR); Byung Mook Weon, Pohang-si (KR)

(73) Assignee: Postech Academy-Industry Foundation (KR)

( * ) Notice: Subject to any disclaimer, the term of this patent is extended or adjusted under 35 U.S.C. 154(b) by 209 days.

(21) Appl. No.: 12/009,157

(22) Filed: Jan. 16, 2008

(65) Prior Publication Data
US 2009/0155365 A1 Jun. 18, 2009

(30) Foreign Application Priority Data
Dec. 14, 2007 (KR) ...................... 10-2007-0131252

(51) Int. Cl.
*A61M 5/00* (2006.01)
*A61K 9/00* (2006.01)
*A61N 5/00* (2006.01)
(52) U.S. Cl. .......................... 424/423; 424/486; 604/20
(58) Field of Classification Search ........................ None
See application file for complete search history.

(56) References Cited
U.S. PATENT DOCUMENTS
7,235,592 B2 6/2007 Muratoglu et al.

2004/0121451 A1* 6/2004 Moritz et al. ............ 435/287.2
2006/0074182 A1* 4/2006 King et al. .................. 524/612
2007/0248674 A1* 10/2007 Del Curto et al. ........... 424/486

FOREIGN PATENT DOCUMENTS
JP 2007-070490 3/2007

OTHER PUBLICATIONS

Kang Moo Huh, et al., "Supramolecular-Structured Hydrogels Showing a Reversible Phase Transition by Inclusion Complexation Between Poly(ethylene glycol) Grafted Dextran and α-Cyclodextrin", Nov. 25, 2001, vol. 34, pp. 8657-8662.

* cited by examiner

*Primary Examiner*—Robert A Wax
*Assistant Examiner*—Danah Al-Awadi
(74) *Attorney, Agent, or Firm*—Harness, Dickey & Pierce, P.L.C.

(57) ABSTRACT

The present invention relates to a method for remotely controlling a sol-gel transition of hydrogels and a method for delivering a drug using the same. More specifically, the invention relates to a method of remotely controlling a sol-gel transition of polyethylene glycol (PEG)-containing hydrogels—three-dimensional networks of crosslinked polymer chains—by X-ray irradiation, and relates to a method for delivering a drug using the same.

9 Claims, 3 Drawing Sheets

METHOD FOR REMOTELY CONTROLLING A SOL-GEL TRANSITION OF HYDROGELS AND METHOD FOR DELIVERING A DRUG USING THE SAME

BACKGROUND OF THE INVENTION

1. Field of the Invention

The present invention relates to a method for remotely controlling a sol-gel transition of hydrogels and a method for delivering a drug using the same. More specifically, the invention relates to a method of remotely controlling a sol-gel transition of polyethylene glycol (PEG)-containing hydrogels—three-dimensional networks of crosslinked polymer chains—by X-ray irradiation, and relates to a method for delivering a drug using the same.

2. Background of the Related Art

Phase transition triggered by external perturbation is quite important for "intelligent materials" and a key issue in diverse fields ranging from biomedicine to chemistry, physics, and materials science.

Hydrogels—three-dimensional networks of crosslinked polymer chains—exhibit transitions in response to perturbations such as electric fields, temperature changes, pH changes, concentration changes, enzymes, electron beams, sound, and light. Hydrogels are actively studied with the objective to develop new technologies to control fluidity, viscoelasticity, solvent volatility, optical transmission, ion transport, and other properties.

Light irradiation is an interesting candidate as a "remote stimulus". However, versatile remote control by ultraviolet and visible light remains a challenge, in particular for thick opaque objects because of low penetration.

SUMMARY OF THE INVENTION

Therefore, the present invention has been made in view of the above problems, and it is the first object of the present invention to provide a method for remotely controlling a sol-gel transition of hydrogels, which offers the important advantage of high penetration, making it applicable to thick objects like a living body such as animal body or human body.

And, it is the second object of the present invention to provide a method for effectively delivering drugs to a target portion in the living body using the same.

To accomplish the first object, according to one aspect of the present invention, there is provided a method for remotely controlling a sol-gel transition of hydrogels, the method comprising the steps of: (a) preparing hydrogels; and (b) irradiating X-rays to the hydrogels so as to trigger a gel-to-sol transition of the hydrogels.

Preferably, the hydrogels are polyethylene glycol (PEG)-containing hydrogels having three-dimensional networks of crosslinked polymer chains.

Preferably, the X-rays are hard X-rays.

Preferably, the hard X-rays are in the energy range of 10-60 keV.

Preferably, the hard X-rays are irradiated for 60 seconds.

Preferably, the gel-to-sol transition of the hydrogels is reversible.

To accomplish the second object, according to another aspect of the present invention, there is provided a method for delivering drugs using a remote control of a sol-gel transition of hydrogels, the method comprising the steps of: (a) preparing a suspension of hydrogels and drugs; (b) administrating the suspension into a living body to transport the suspension to a target portion of the living body; and (c) irradiating X-rays to the transported suspension so as to trigger a gel-to-sol transition of the hydrogels in the transported suspension, and thereby releasing the drugs from the transported suspension into the target portion of the living body.

Preferably, the hydrogels are polyethylene glycol (PEG)-containing hydrogels having three-dimensional networks of crosslinked polymer chains.

Preferably, the X-rays are hard X-rays.

Preferably, the hard X-rays are in the energy range of 10-60 keV.

Preferably, the hard X-rays are irradiated for 60 s.

Preferably, the living body is an animal body or a human body.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIG. 1$a$ shows evolution of the capillary surface shape with the X-ray irradiation time—showing that the irradiation triggers a transition from a gel (irregular shaped) to a sol (spherical shaped) state in our PEG hydrogel. The real-time synchrotron X-ray imaging provides direct evidence of the hydrogel gel-to-sol transition. The scale bar is 100 μm. FIG. 1$b$ shows decrease of the capillary radius with the X-ray irradiation time. This decrease corresponds to a reduction of the viscosity underlying the gel-to-sol transition. The reciprocal time dependence of the radius, $r \propto t^{-1}$ (solid line), predicts a reciprocal time dependence of the viscosity, $\eta \propto t^{-1}$, through the relations of $r \propto \gamma \propto \eta$;

DETAILED DESCRIPTION OF THE PREFERRED EMBODIMENT

The preferred embodiments of the invention will be hereafter described in detail, with reference to the accompanying drawings.

In the preferred embodiments of the present invention are used experimental conditions as follows:

X-ray irradiation: We used synchrotron X-rays at the 7B2 beamline of the Pohang Light Source (PLS) in Pohang, Korea. Spatially-coherent synchrotron X-rays in the photon energy range of 10-60 keV were applied not only to the irradiation of hydrogel but also to real-time phase contrast X-ray imaging of the transitions. The scintillator-specimen distance was set at 150 mm to optimize phase contrast. The beam spot size was 0.58×0.44 mm$^2$ and the microradiology spatial resolution was 0.5 μm. Sequential real-time images were taken with an acquisition time of 100 ms.

Hydrogel: The PEG-containing hydrogel; purchased from Dayo Medical (Seoul, Korea), was ProGel-II (Korean Patent No. 0360278) and was crosslinked with PEG (2.0% w/w, MW 600) through triethanolamine (1.2% w/w) buffer.

Viscometry: The falling ball test was performed using a silica ball (130 μm in diameter) in the hydrogel medium. Accurate measurements of the falling distance (s) and velocity (v=ds/dt) were performed using real-time synchrotron X-ray imaging. The viscosity was evaluated through the equation $\eta=(d^2/18\ v)\ \Delta\rho g$ from the ball diameter (d), the density difference between the ball and the medium ($\Delta\rho$), and the gravitational acceleration (g).

Model drug: The model drug was a dense mixture of hydrogel (ProGel-II, Dayo Medical Co., Korea) and melamine microspheres (9.2 μm in diameter, 50 mg/ml, Corpuscular Inc., Germany). The drug was initially insoluble in iodinated water (loxithalamate, Telebrix 35, 350 mgI/ml, Guerbet, France). The heating by X-ray irradiation was negligible in our case. Temperature measurements by an infrared thermometer revealed a small temperature increase $\delta T$~1.0 K during X-ray irradiation. All experiments were conducted at room temperature (25° C.).

We present here the first evidence of an X-ray-triggered sol-gel transition in hydrogels. The transition is triggered by a brief irradiation with hard X-rays (10-60 keV) and is attributed to the strengthening of hydrogen bonds by X-ray radiolysis of water. Real-time synchrotron X-ray imaging (from the PLS 7B2 beamline, Pohang, Korea) provided direct evidence of the sol-gel transition. The present invention opens a remote, versatile control way of sol-gel transitions using X-ray irradiation.

One embodiment of the present invention relates to a method for remotely controlling a sol-gel transition of hydrogels, the method comprising the steps of: (a) preparing hydrogels; and (b) irradiating X-rays to the hydrogels so as to trigger a gel-to-sol transition of the hydrogels. Preferably, the hydrogels are polyethylene glycol (PEG)-containing hydrogels having three-dimensional networks of crosslinked polymer chains.

Figure 1A:
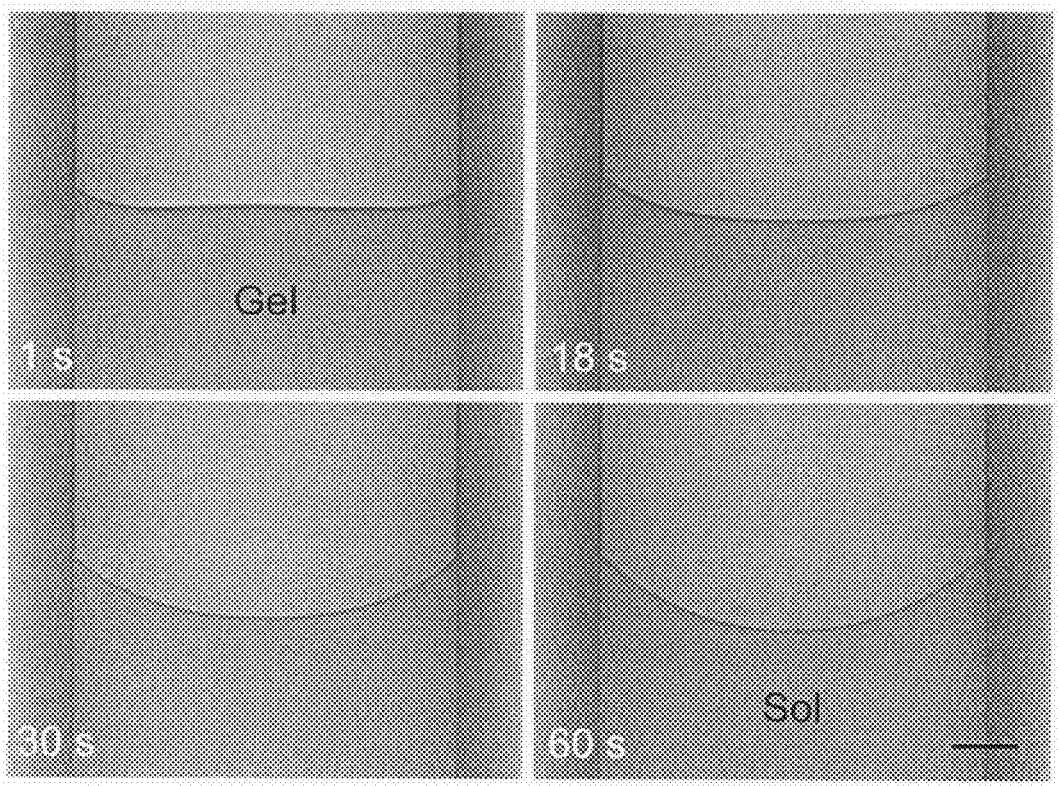
FIG. 1 shows the results of capillary test during X-ray irradiation according to one embodiment of the present invention.

FIG. 1a shows the experimental evidence for a gel-to-sol transition of a PEG hydrogel in an open capillary tube triggered by X-ray irradiation according to one embodiment of the present invention. The capillary surface shape; monitored in real time with synchrotron X-ray microradiography, changes from non-spherical (gel) to spherical (sol) during the X-ray irradiation. The capillary radius decrease provides direct evidence for the hydrogel gel-to-sol transition.

Figure 1B:
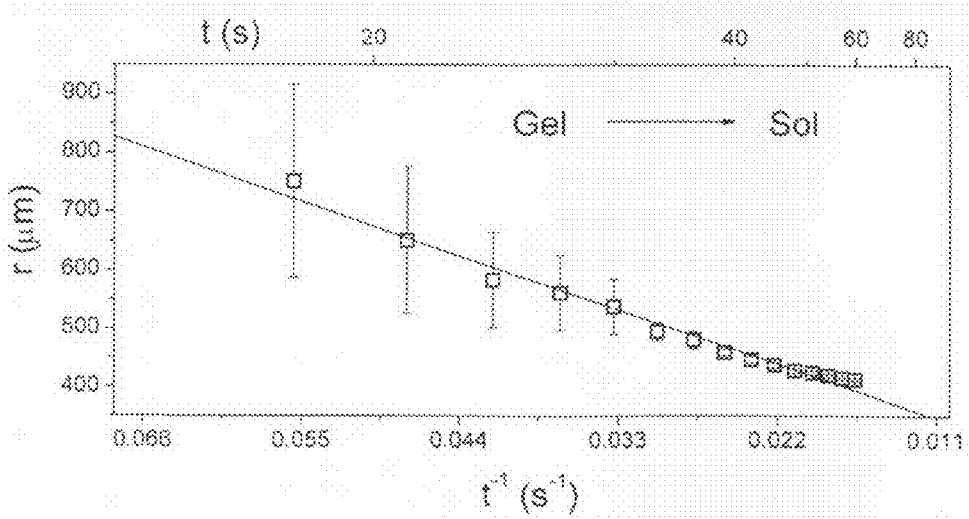

In FIG. 1b, we see that the capillary radius gradually decreases with the X-ray irradiation time according to one embodiment of the present invention. This decrease is explained by the surface tension depression caused by the X-ray radiolysis of water in the hydrogel. The gel phase almost completely changes into the sol phase after approximately 60 seconds of irradiation, as revealed by the marked sphericity. After the X-ray irradiation stops, the hydrosol resolidifies into hydrogel showing that the transition is reversible.

We would now like to discuss in more detail the physical origin of the capillary radius decrease (FIG. 1b). The capillary pressure is given by the Young-Laplace equation: $p=2\gamma/r$ with $\gamma$ being the surface tension and r the capillary radius. From this, the surface tension is simply given by $\gamma=rp/2$, that is, $\gamma\propto r$. Here the surface tension $\gamma$ is only a function of r, since p is constant in an open capillary tube. Considering that the surface tension is also related to the viscosity for a liquid as $\gamma\propto\eta$, we can derive a simple link between the capillary radius and the viscosity as $r\propto\eta$. This implies that the capillary radius decrease in FIG. 1b is directly related to a reduction in the viscosity. Here the reciprocal time dependence of the radius, $r\propto t^{-1}$ (solid line), predicts a reciprocal time dependence of the viscosity, $\eta\propto t^{-1}$.

Figure 2:
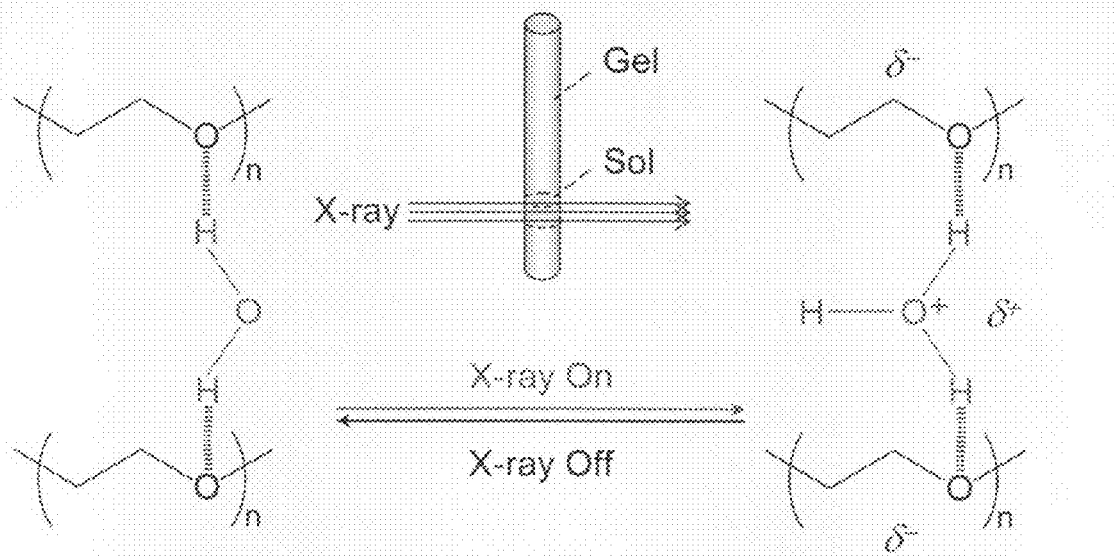
FIG. 2 shows a possible X-ray-triggered gel-to-sol transition mechanism according to one embodiment of the present invention. The phenomenon is attributed to the increased solubility of the PEG hydrogel in water due to the strengthening of hydrogen bonding.

FIG. 2 shows a possible hypothesis of the gel-to-sol transition mechanism induced by X-ray irradiation according to one embodiment of the present invention. The most important aspect in the X-ray irradiation of water is the generation of hydrogen-based species (e.g., $H_2$, $H_3O^+$, and $H_2O_2$). The hydrogen bonding between the PEG chains and the water molecules is likely to be strengthened by such species. This explains the X-ray-triggered phase transition because the water solubility of the PEG hydrogel is increased by the enhanced hydrogen bonding. On the other hand, the radiation-induced crosslinking or degradation is negligible in the hydrogel with a small molecular weight of 600, considering the lower photon energies of the X-rays used here (~keV) with respect to gamma-ray (~MeV).

Figure 3:
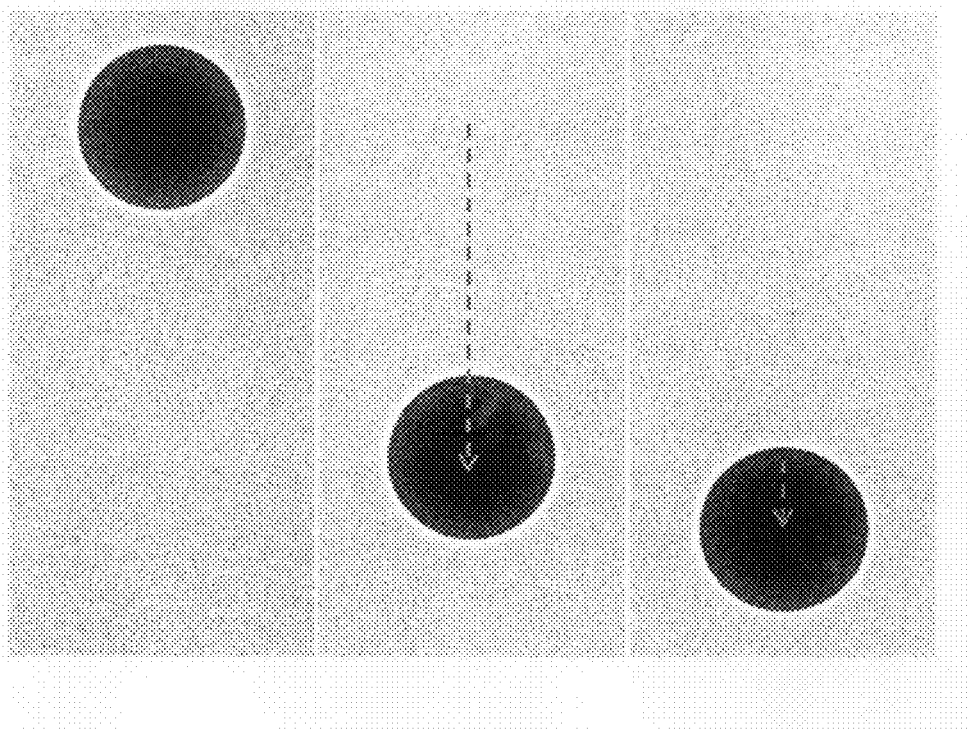
FIG. 3 shows the results of falling ball test during X-ray irradiation according to one embodiment of the present invention. A silica ball (130 μm in diameter), initially at rest in the hydrogel medium, is allowed to fall under the influence of gravity for 90 s during X-ray irradiation: the high speed confirms the gel-to-sol transition. In contrast, a small displacement occurs during the 90 s period after the X-ray irradiation stops, indicating a reverse sol-to-gel transition. These results confirm the interpretation of the capillarity tests and demonstrate the reversibility of the X-ray-induced sol-gel transitions.

FIG. 3 demonstrates the reversibility of the transition with a falling ball test during X-ray irradiation according to one embodiment of the present invention. A silica ball (130 μm in diameter), initially at rest in the hydrogel medium, is allowed to fall under the influence of gravity in the presence of X-ray irradiation for 90 seconds. A large free-falling displacement is a manifestation of the gel-to-sol transition of the X-ray irradiated medium. In contrast, after the X-ray irradiation stops, the displacement in the subsequent 90 s is much smaller, indicating a reversed sol-to-gel transition.

Figure 4:
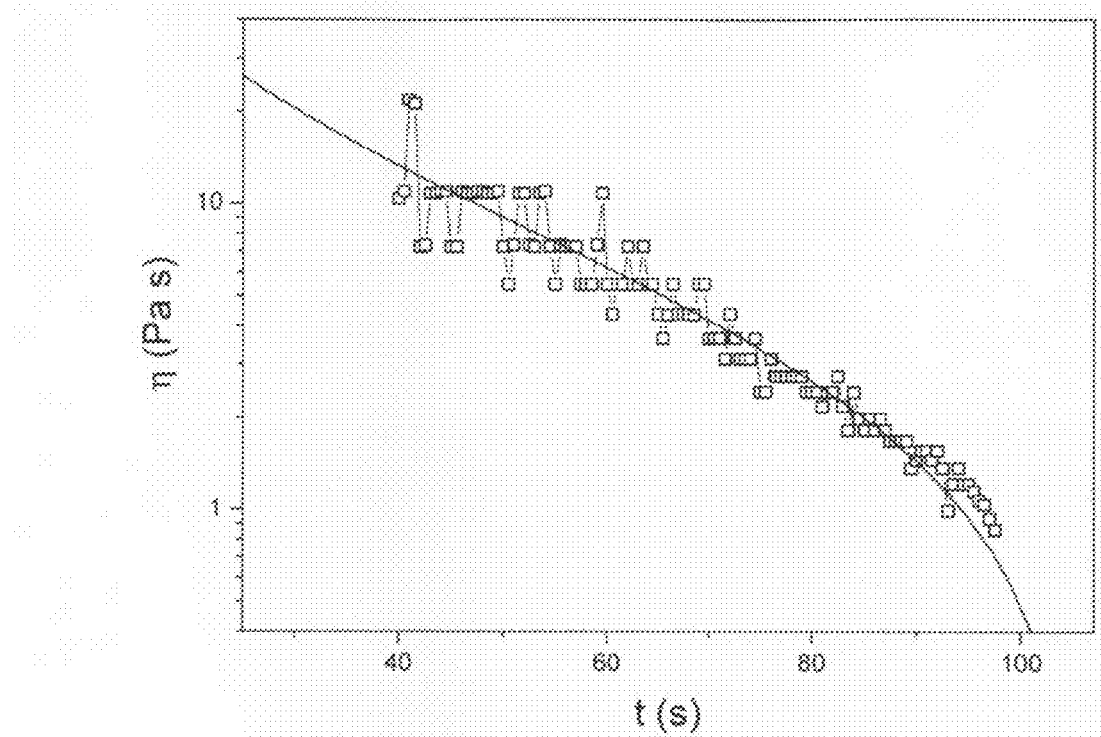
FIG. 4 shows viscosity changes during the X-ray irradiation according to one embodiment of the present invention. The reciprocal time dependence of the viscosity, $\eta \propto t^{-1}$, is consistent (solid line) with the experimental data, as expected from $r \propto t^{-1}$ and $r \propto \eta$. The reduction in the viscosity provides rheological evidence of the X-ray-induced gel-to-sol transition.

The viscosity changes during. X-ray irradiation were also measured with the falling ball test, providing further evidence for the gel-to-sol transition. Accurate measurements of the falling distance (s) and velocity (v=ds/dt) were performed using real-time synchrotron X-ray imaging. The viscosity was then evaluated through the equation $\eta=(d^2/18\ v)\ \Delta\rho g$ from the ball diameter (d), the density difference between the ball and the medium ($\Delta\rho$), and the gravitational acceleration (g). The X-ray-induced decrease in the hydrogel viscosity is illustrated in FIG. 4 and is in good agreement with the typical viscosity behavior during sol-gel transitions of hydrogels, providing a rheological corroboration of the capillary tests. The reciprocal time dependence of the viscosity (solid line), $\eta\propto t^{-1}$, is consistent with the capillary experiment in FIG. 1b. The reduction in the viscosity during X-ray irradiation also implies that the X-ray-induced transition is not related to crosslinking of hydrogels.

Our present results indicate that X-ray irradiation is a good alternative to control sol-gel transitions for polyethylene glycol (PEG)-containing hydrogels. Such hydrogels were widely studied for biotechnological applications because of their high biocompatibility, hydrophilicity, and versatility. X-ray irradiation offers the important advantage of high penetration, making it applicable to thick objects like the human body.

The possibility to remotely control the X-ray-triggered transition can be exploited for new drug delivery strategies as below.

Another embodiment of the present invention relates to a method for delivering drugs using a remote control of a sol-gel transition of hydrogels, the method comprising the steps of: (a) preparing a suspension of hydrogels and drugs; (b) administrating the suspension into a living body to transport the suspension to a target portion of the living body; and (c) irradiating X-rays to the transported suspension so as to trigger a gel-to-sol transition of the hydrogels in the transported suspension, and thereby releasing the drugs from the transported suspension into the target portion of the living body. The step (b) may be perform with any conventional drug administration, for example, an oral administration, injection administration, etc.

Figure 5:
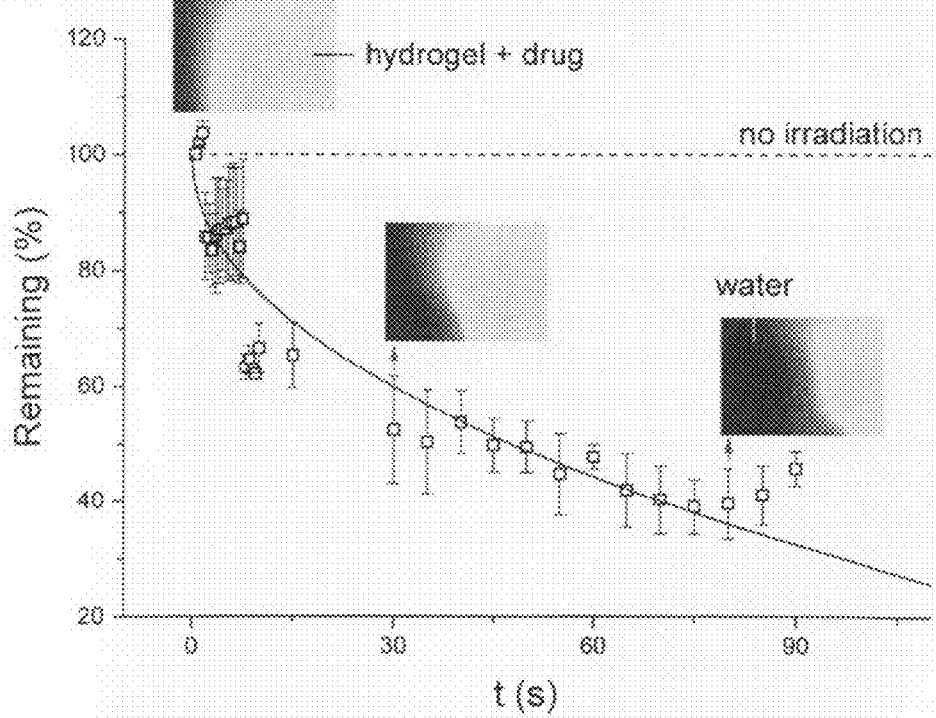
FIG. 5 shows X-ray-triggered release of a model drug compound consisting of a dense suspension of hydrogel (reservoir) and melamine microspheres (drug) according to another embodiment of the present invention. The cumulative release curve is the remaining percentage of the hydrogel plus drug. The release kinetics ($\sim t^{0.47 \pm 0.04}$) indicates a diffusion-controlled release (solid line). These results support the idea of a remote control of drug release by X-ray irradiation.

FIG. 5 shows evidence of X-ray-induced release in a model drug compound according to another embodiment of the present invention. The model drug is a dense suspension of hydrogel and melamine microspheres. The drug is initially insoluble in iodinated water but is rapidly released into water during the X-ray irradiation. This is demonstrated by the snapshot images that show the X-ray-opaque iodinated water (blue) and the X-ray-transparent model drug suspension (green): the drug suspension volume decreases during irradiation, revealing release into water. The release kinetics ($\sim t^{0.47\pm 0.04}$) corresponds to a typical diffusion-controlled release. The release of the drug (modeled as melamine microspheres) can be attributed to the enhanced solubility of PEG caused by the X-ray irradiation, as illustrated in FIG. 2.

In conclusion, we demonstrated the first evidence of an X-ray-triggered sol-gel transition in polyethylene glycol (PEG)-based hydrogels. The transition, triggered by a brief irradiation with hard X-rays (10-60 keV), was attributed to the strengthening of hydrogen bonds by X-ray radiolysis of water. Direct and rheological evidence of the reversible sol-gel transition was provided by real-time synchrotron X-ray imaging. X-ray-triggered release in a model drug compound supported the idea of a remote control of drug release by X-ray irradiation. Because of its high penetration, X-ray irradiation can be a remote, versatile stimulus for phase transitions in intelligent materials, opening up new and interesting technological opportunities.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A method for remotely controlling a sol-gel transition of hydrogels, the method comprising the steps of:
   (a) preparing hydrogels containing polyethylene glycol and water; and
   (b) irradiating the hydrogels with X-rays so as to trigger a gel-to-sol transition of the hydrogels.

2. The method according to claim 1, wherein the X-rays are hard X-rays.

3. The method according to claim 2, wherein the hard X-rays are in the energy range of 10~60 keV.

4. The method according to claim 3, wherein the hard X-rays are irradiated for 60 seconds.

5. The method according to claim 1, wherein stopping the irradiating reverses the gel-to-sol transition of the hydrogels.

6. A method for remotely controlling a sol-gel transition of a hydrogel, the method comprising the steps of:
   (a) preparing a hydrogel comprising polyethylene glycol and water;
   (b) irradiating the hydrogel with X-rays so as to trigger a gel-to-sol transition of the hydrogel; and
   (c) stopping the irradiating to reverse the gel-to-sol transition of the hydrogel.

7. The method according to claim 6, wherein the X-rays are hard X-rays.

8. The method according to claim 7, wherein the hard X-rays are in the energy range of 10~60 keV.

9. The method according to claim 7, wherein the hard X-rays are irradiated for 60 seconds.

* * * * *